US012576218B2

(12) United States Patent
    Bartels et al.

(10) Patent No.: US 12,576,218 B2
(45) Date of Patent: Mar. 17, 2026

(54) VALVE

(71) Applicant: INVOX BELGIUM NV, Diepenbeek (BE)

(72) Inventors: Frank Bartels, Hattingen (DE); Juergen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 1189 days.

(21) Appl. No.: 17/601,928

(22) PCT Filed: Apr. 14, 2020

(86) PCT No.: PCT/EP2020/060403
    § 371 (c)(1),
    (2) Date: Oct. 7, 2021

(87) PCT Pub. No.: WO2020/212313
    PCT Pub. Date: Oct. 22, 2020

(65) Prior Publication Data
    US 2022/0143328 A1      May 12, 2022

Related U.S. Application Data

(60) Provisional application No. 62/833,977, filed on Apr. 15, 2019.

(30) Foreign Application Priority Data

Apr. 15, 2019    (EP) ..................................... 19169154

(51) Int. Cl.
    *A61M 11/00*        (2006.01)
    *A61M 15/00*        (2006.01)
            (Continued)

(52) U.S. Cl.
    CPC ...... *A61M 11/007* (2014.02); *A61M 15/0065* (2013.01); *B05B 11/026* (2023.01);
            (Continued)

(58) Field of Classification Search
    CPC ... A61M 11/007; A61M 11/006; B05B 11/10; B05B 11/109; B05B 11/1004;
            (Continued)

(56) References Cited

U.S. PATENT DOCUMENTS 5,152,434 A      10/1992  Birmelin
    5,161,574 A  *  11/1992  Chacin .................... F16K 15/06
                                                                137/533.17
            (Continued)

FOREIGN PATENT DOCUMENTS

CN          1534203 A      10/2004
    CN      101255927 A        9/2008
            (Continued)

OTHER PUBLICATIONS

Erb et al. "Antiasthmatic Agents", https://onlinelibrary.wiley.com/doi/full/10.1002/14356007.a02_453.pub2?a02_453-eo-2013=accessed on Oct. 2024 (Year: 2010).*
            (Continued)

*Primary Examiner* — Joseph D. Boecker
*Assistant Examiner* — Jaeick Jang
(74) *Attorney, Agent, or Firm* — Synergy IP Group AG

(57)                ABSTRACT

A valve for an inhalation device for generation of an aerosol of a medically active liquid may include: a housing, inside this housing a reservoir for storing medically active liquid, downstream from this reservoir a pumping unit for generation of a pressure connected to a means for the delivery of mechanical energy to said pumping unit, and downstream said pumping unit a nozzle; wherein the pumping unit includes a hollow cylindrical part and a piston, the cylin-
            (Continued)

drical part having an interior space configured to receive an end portion of said piston, wherein said cylindrical part and said piston are linearly moveable relative to one another such as to form a pumping chamber having a variable volume.

20 Claims, 4 Drawing Sheets

(51) Int. Cl.
  *B05B 11/02*     (2023.01)
  *B05B 11/10*     (2023.01)

(52) U.S. Cl.
  CPC .. *B05B 11/1091* (2023.01); *A61M 2202/0468* (2013.01); *A61M 2205/0216* (2013.01)

(58) Field of Classification Search
  CPC .......... B05B 11/1091–97; B05B 11/06; B05B 11/061; B05B 11/062; B05B 11/0062; B05B 11/0075; B05B 11/007; B05B 11/1067; B05B 11/1069; B05B 11/107; B05B 11/1071; F16K 15/06
  See application file for complete search history.

(56) References Cited

U.S. PATENT DOCUMENTS

| | | | |
|---|---|---|---|
| 5,349,984 A | 9/1994 | Weinheimer et al. | |
| 5,429,275 A | 7/1995 | Katz | |
| 5,894,960 A | 4/1999 | Rodden, Jr. | |
| 5,964,416 A * | 10/1999 | Jaeger | A61M 15/0065 |
| | | | 222/402 |
| 6,189,739 B1 * | 2/2001 | von Schuckmann | |
| | | | B05B 11/1059 |
| | | | 222/321.6 |
| 9,757,750 B2 * | 9/2017 | Holakovsky | B05B 11/026 |
| 11,035,066 B2 * | 6/2021 | Nam | D06F 37/26 |
| 2002/0166876 A1 | 11/2002 | Masuda | |
| 2004/0068222 A1 * | 4/2004 | Brian | A61M 11/002 |
| | | | 604/152 |
| 2004/0194828 A1 | 10/2004 | Landhuis | |
| 2008/0017256 A1 * | 1/2008 | Thomas | F16K 15/023 |
| | | | 137/529 |
| 2011/0290242 A1 * | 12/2011 | Bach | A61M 15/0036 |
| | | | 128/200.21 |
| 2012/0138049 A1 | 6/2012 | Wachtel | |
| 2014/0182716 A1 | 7/2014 | Yamada et al. | |
| 2020/0324306 A1 * | 10/2020 | Bilton | B05B 11/1026 |

FOREIGN PATENT DOCUMENTS

| | | |
|---|---|---|
| CN | 103899382 A | 7/2014 |
| EP | 0627230 B1 | 2/2000 |
| JP | 2002066401 A | 3/2022 |
| KR | 100615036 B1 | 8/2006 |
| KR | 101486012 B1 | 2/2015 |
| WO | 2008011240 A2 | 1/2008 |
| WO | 2010133294 A2 | 11/2010 |
| WO | 2015191478 A1 | 12/2015 |
| WO | 2018189424 A1 | 10/2018 |
| WO | 2018197730 A1 | 11/2018 |

OTHER PUBLICATIONS

Kim et al. "Overlap between Asthma and COPD", https://pmc.ncbi.nlm.nih.gov/articles/PMC2946698/#:~:text=There%20is%20a%20marked%20increase,lavage%20fluid%20and%20induced%20sputum.&text=Given%20that%20asthma%20and%20COPD,they%20present%20common%20therapeutic%20targets accessed on Oct. 2024 (Year: 2010).*
Written Opinion of the International Searching Authority of International Patent Application No. PCT/EP2020/060403, Jun. 12, 2020, 7.
EN translation of the Search report of CN113677386 dated May 29, 2024.
EP examination report of Mar. 7, 2024.
TW Office action of Aug. 10, 2023.

* cited by examiner

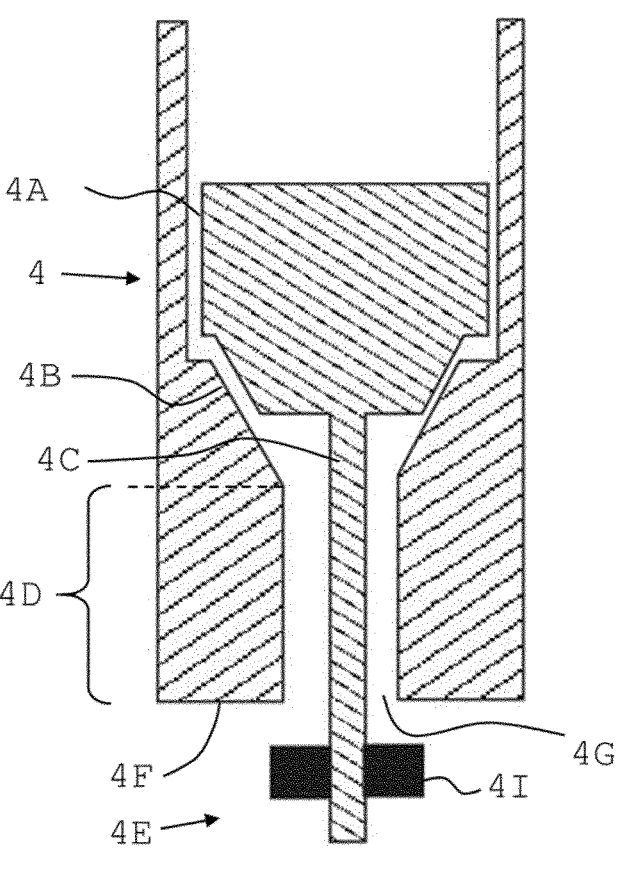
4A
4
4B
4C
4D
4F
4E
4G
4I
FIG. 7
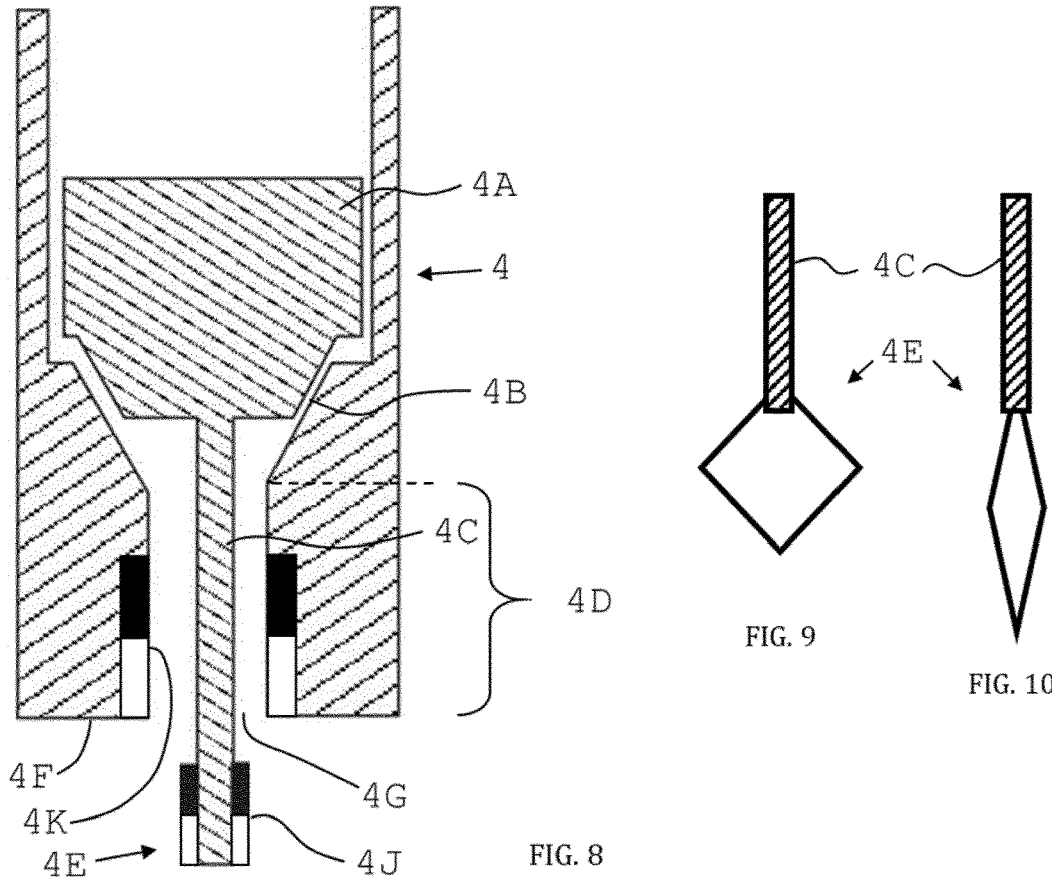
4A
4
4B
4C
4D
4F
4K
4E
4G
4J
FIG. 8
4C
4E
FIG. 9
FIG. 10

VALVE

CROSS REFERENCE TO RELATED APPLICATIONS

This application is a United States National Stage Application filed under 35 U.S.C. § 371 claiming the benefit of PCT Application No. PCT/EP2020/060403, filed on Apr. 14, 2020, which claims priority to and the benefit of European Application No. 19169154.2, filed on Apr. 15, 2019, and U.S. Provisional Application Ser. No. 62/833,977, filed on Apr. 15, 2019, all of which are incorporated herein by reference in their entireties.

FIELD OF THE INVENTION

The invention relates to the field of inhalation devices for liquids. In particular, the invention relates to a pumping unit for an inhalation device having a piston which moves relative to a pumping chamber in order to generate pumping pressure.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle. A pumping unit is defined as a unit, device or component capable of moving or compressing a fluid material and that comprises at least one pumping chamber, and optionally further comprises auxiliary components as well, such as a body, interfaces, and the like. By means of the pumping unit, the liquid is drawn in a discrete amount, i.e. not continuously, from the reservoir, and fed to the nozzle. The pumping unit works without propellant and generates pressure mechanically.

This inhalation device makes use of a fixed pumping chamber, into which a moveable and hollow piston can be inserted in order to decrease the interior volume of said chamber, thus increasing the pressure both in said chamber and the inside of the piston, eventually leading to atomization of the liquid from the nozzle. By again extracting the piston from the chamber, its interior volume is increased, and the resulting negative pressure leads to drawing liquid from the reservoir into the chamber, such that a new atomizing cycle can begin.

An improvement of such an inhalation device is disclosed in international patent application WO 2018/197730 A1, filed by the same applicant as the present invention, the content of which is incorporated herein in its entirety. According to this improvement, the inhalation device provides a fixed piston and a moveable pumping chamber with a hollow cylindrical part. By pushing the cylindrical part onto the hollow piston, the pressure inside the pumping chamber is increased and the liquid is pressed out of the nozzle. By pulling the cylindrical part from the piston, the pressure becomes negative and fresh liquid is drawn into the increasing volume of the chamber.

In order to avoid backflow of liquid from the pumping chamber into the reservoir during the high-pressure phase, typically, a check valve is located fluidically between pumping chamber and reservoir. When the pressure in the pumping chamber rises, the valve closes such that pressurized liquid can only flow towards the nozzle.

As a valve, a ball valve is preferably used, comprising a moveable body, and a seat which is shaped accordingly to provide sufficient leak tightness when the body is pressed against the seat during the high-pressure phase. In contrast, in the refilling (low-pressure) phase, the body moves away from the seat, allowing liquid to pass the valve from the reservoir into the pumping chamber. The region, or volume, in which the body must be moveable in order to fulfill its task is subsequently called "working region".

However, measures must be taken in order to avoid the moveable body from leaving the working region and entering the pumping chamber, since such uncontrolled movement could clog the device and/or destroy the often delicate, since very small, and precisely formed body. For this, the body is located inside a "cage" which is formed by an obstruction which is located at the downstream end of the working region.

When the low-pressure phase starts, the body is at this point spaced furthermost away from the seat Thus, the amount of liquid volume which is located between seat and body will pass the valve seat before the ball, transported backwards by the liquid, eventually contacts the seat, thus closing the valve. This amount of liquid does not contribute to the nebulization, since it is transported forth and back; therefore, it can be referred to as a "dead volume", which, in general, should be minimized. While the distance must have a certain minimal size in order to provide a sufficiently low flow resistance, a too great gap between body and seat does not further decrease the flow resistance in downstream direction, but it increases, when the liquid flows in upstream direction, the amount of said liquid volume during closure of the valve, i.e. aforementioned "dead volume". Therefore, a position of the obstruction rather close to the body, leaving only a gap as small as necessary between body and seat when the valve is open, is preferred.

The obstruction can be formed by simply indenting the outer wall of the pumping chamber, if the same is made from a deformable material such as metal or a thermoplastic synthetic. An advantage of such a simple solution is that no additional components are necessary. However, the position and depth of the indentation must be precisely controlled which is difficult to achieve and to reproduce. Also, forming the indentation requires an additional fabrication step.

Another solution to provide an obstruction is based on the insertion of an additional mechanical component such as a ring or grating that leaves one or more openings smaller than the effective diameter of the body. The component is located downstream the body at the desired end of the working volume. The interior diameter of the tube in which the body is movably arranged is therefore reduced, and the body cannot pass beyond the obstructing component. An advantage of using an additional mechanical component is the improved control of the size of the working region. A disadvantage of this solution is that forming and precisely inserting such a component is difficult to achieve. Further, for said insertion, at least one additional fabrication step is required. Also, if no measures are taken to firmly keep the component in place, it is possible that the same moves along the tube, resulting in either an increase or decrease of the volume of the working region. Thus, such a movement can result in an undesired increase of the "dead volume", or an inhibition of any body movement so that the valve is continuously closed.

OBJECT OF THE INVENTION

It is an object of the invention to provide a device that avoids the drawbacks of the known art More specifically, the valve shall have a precisely controllable, stable size of working region. The dead volume shall be easy to minimize, and as little additional working steps as possible shall be required in order to achieve the improved valve.

SUMMARY OF THE INVENTION

According to a first aspect, the present invention provides for an inhalation device for generation of an aerosol of a medically active liquid and for the inhalative administration of the aerosol of said medically active liquid, said inhalation device comprises:

a housing, inside this housing a reservoir for storing said medically active liquid, downstream this reservoir a pumping unit for generation of a pressure connected to a means for the delivery of mechanical energy to said pumping unit, and downstream said pumping unit a nozzle;

wherein the pumping unit comprises a hollow cylindrical part and a piston, the cylindrical part having an interior space configured to receive an end portion of said piston, wherein said cylindrical part and said piston are linearly moveable relative to one another such as to form a pumping chamber having a variable volume;

the inhalation device further comprising a check valve such as to allow liquid flow in the downstream direction and prevent liquid flow in the opposite direction, the valve comprising a moveable body and a seat arranged upstream the body, the seat being arranged at a downstream end of a hollow seat extension section having an upstream opening, and wherein the check valve's body comprises on its side facing the seat a protrusion which extends through the seat and past said opening of said hollow seat extension section, the protrusion being dimensioned to leave a gap between its lateral surface and an inside of said hollow seat extension section, wherein further, the upstream end of said protrusion is configured to mechanically interact with an upstream end of said hollow seat extension section such as to being blocked from entering said hollow seat extension section, thus limiting movement of the body in downstream direction.

In a second aspect, the present invention provides for an inhalation device according to the first aspect of the invention for use in the treatment or prevention of a respiratory disorder by inhalative administration of an aerosol of a medically active liquid.

In a third aspect, the present invention provides for the use of an inhalation device according to the first aspect of the invention, for the prevention or treatment of a respiratory disorder.

In a fourth aspect, the present invention relates to a method of treating a subject suffering from a lung disease or condition, the method comprising a step of administering a pharmaceutical composition in nebulized (aerosolized) form to said subject using a inhalation device according to the first aspect of the invention.

BRIEF DESCRIPTION OF THE FIGURES

FIG. 7 shows a schematic of the cross section of a second embodiment of a check valve comprised by the inhalation device according to the invention;

FIG. 8 shows a schematic of the cross section of a third embodiment of a check valve comprised by the inhalation device according to the invention;

FIGS. 9, 10 show an embodiment of the upstream end of protrusion of the check valve comprised by the inhalation device according to the invention.

DESCRIPTION OF THE INVENTION

Figure 1:
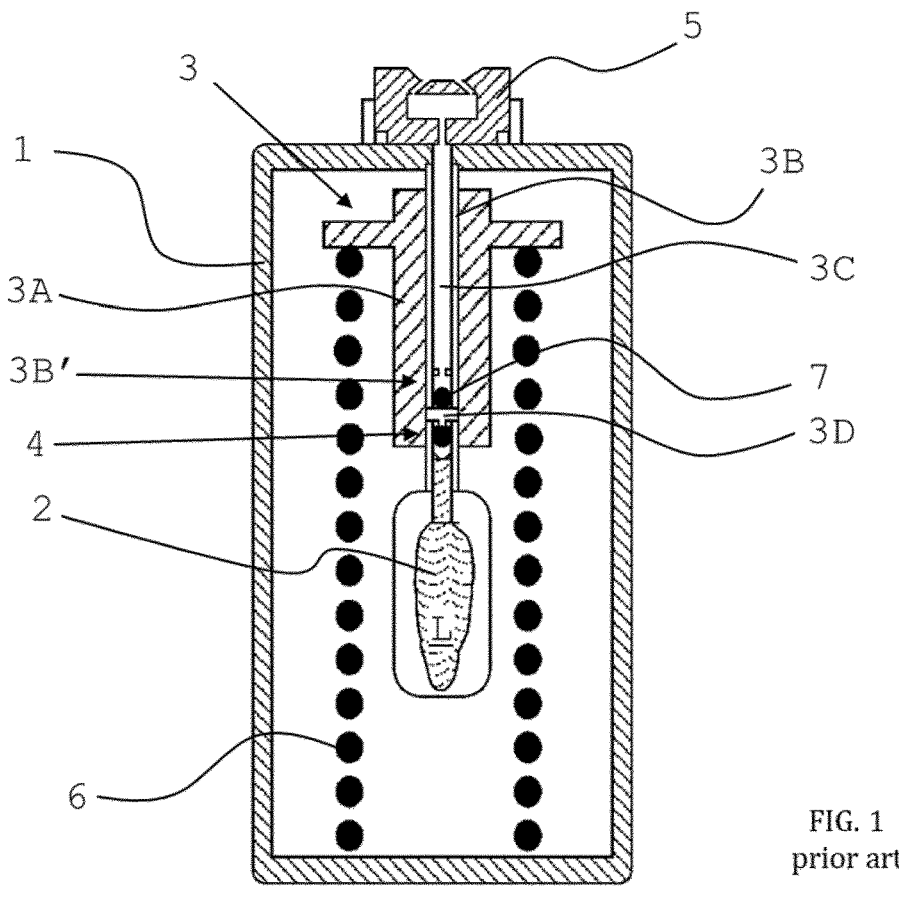
FIG. 1 shows schematically a nebulizer for medically active liquids prior to its first use.

Introductorily, some definitions of terms are given which are used throughout the description and claims. The definitions should be used to determine the meaning of the respective expressions unless the context requires a different meaning.

An "inhaler" or "inhalation device" is a device which is configured and adapted for the generation of an inhalable mist, vapor, or spray.

"Atomization" and "nebulization" in the context of inhalers means the generation of fine, inhalable droplets of a liquid. The typical dimensions of atomized droplets are in the range of several microns.

An "aerosol" is a dispersion of a solid or liquid phase in a gas phase. The dispersed phase, also termed the discontinuous phase, is comprised of multiple solid or liquid particles. The aerosol generated by the inhalation device of the invention is a dispersion of a liquid phase in the form of inhalable liquid droplets in a gas phase which is typically air. The dispersed liquid phase may optionally comprise solid particles dispersed in the liquid.

A "liquid" is a fluid material capable of altering its shape to that of a container which holds the liquid but retains a nearly constant volume independent of pressure. A liquid may represent a monophasic liquid solution or a dispersion with a continuous liquid phase and a dispersed phase which may or may not be liquid.

A "plurality" means two or more.

As used herein, the term "comprising" and related terms "comprise" or "comprises" are to be understood that features additional to the features prefaced by the term may be present. Conversely, the term "consists" and related terms would be understood as meaning that no other features, other than those prefaced by the term are present, and if present, only in trace or residual amounts such as to confer no technical advantage or relevance in respect of the object of the invention.

"Interior" means inside, but also, oriented towards the inside; "Exterior" means outside, but also, oriented towards the outside.

A "nozzle" is a unit that serves for the atomization/nebulization of liquid. Generally, the term means the unit in its entirety. However, a nozzle can comprise one or multiple sets of individual, identical or different sub-units. A nozzle may have a plurality of ejection channels for emitting the liquid(s).

The "main axis" of a nozzle is its central axis parallel or collinear to the direction into which the bulk of the emitted aerosol travels after leaving the nozzle.

A "horizontal" plane is a plane that is perpendicular to the main axis.

The term "upstream" as used herein means towards direction of the reservoir.

The term "downstream" as used herein means towards the direction of the nozzle.

Further definitions are provided in the subsequent description.

The object underlying the present invention is solved, in the first aspect, by an inhalation device for generation of an aerosol of a medically active liquid and for the inhalative administration of the aerosol of said medically active liquid, said inhalation device comprising:

a housing, inside this housing a reservoir for storing said medically active liquid, downstream this reservoir a pumping unit for generation of a pressure connected to a means for the delivery of mechanical energy to said pumping unit, and downstream said pumping unit a nozzle;

wherein the pumping unit comprises a hollow cylindrical part and a piston, the cylindrical part having an interior space configured to receive an end portion of said piston, wherein said cylindrical part and said piston are linearly moveable relative to one another such as to form a pumping chamber having a variable volume;

the inhalation device further comprising a check valve such as to allow liquid flow in the downstream direction and prevent liquid flow in the opposite direction, the valve comprising a moveable body and a seat arranged upstream the body, the seat being arranged at, and fluidically connected with, a downstream opening of a hollow (i.e. bore-hole like) seat extension section having also an upstream opening, and wherein the check valve's body comprises on its side facing the seat a protrusion which extends through the seat and past said upstream opening of said hollow seat extension section, the protrusion being dimensioned to leave a gap between its lateral surface and an inside of said hollow seat extension section, wherein further, the upstream end of said protrusion is configured to mechanically interact with an upstream end, or upstream end region, of said hollow seat extension section such as to being blocked from entering said hollow seat extension section, thus limiting movement of the body in downstream direction.

With regard to the feature of relative movement of hollow cylindrical part and piston of the pumping unit, this may be preferably achieved by that the cylindrical part is attached to the housing of the present inhalation device and the piston can be moved therein, or by that the piston is attached to the housing and the cylindrical part can be moved therein, or both parts are moveable with respect to the housing as well as each other. For further explanations, reference is made to the description below as well as the Figures.

The object is further solved by the further aspects of the invention described further below. Advantageous embodiments are described in the respective dependent claims, the subsequent description, as well as the accompanying Figures.

The inhalation device according to the present invention is intended to be used for the generation of an aerosol from medically active liquids for inhalation therapy. In particular, the inhalation device is adapted for the dose-wise generation and emission of nebulized aerosols suitable for the pulmonary delivery of medically active ingredients. The inhalation device according to the present invention comprises a valve or, more specifically, a check valve as described in further detail below.

Typically, such an inhalation device comprises a housing, inside this housing a reservoir for storing a liquid, such as a medically active liquid. The reservoir may have a capacity for storing a liquid volume of about 1 mL to about 100 mL, and preferably of about 2 mL to about 50 mL, and particularly preferred of about 4 mL to about 10 mL, e.g. of about 4.5 mL. Downstream of this reservoir, the device comprises a pumping unit which is preferably based on the principle of a piston pump or plunger pump, and downstream said pumping unit a nozzle. Obviously, the pumping unit is fluidically connected to both the nozzle and the reservoir.

The pumping unit of the inhalation device serves for generation of a pressure and is connected to, or driven by, a means for the delivery of mechanical energy to said pumping unit. By said means, the pumping unit may be supplied with a predefined, relatively constant peak amount of mechanical energy which is sufficient for generating the required emission pressure. As a result, the emission or delivery performance of the device is exceptionally reproducible, compared with devices where the emission pressure is provided manually by the user, and thus, varies substantially during the emission phase.

More specifically, said pumping unit comprises a hollow cylindrical part having an interior space. It is noted that the term "cylindrical part" refers to a part having a cylindrical internal surface; the outside as well as an inside portion which does not come in contact with components being relatively moveable to the cylindrical part do not have to be cylindrical.

The pumping unit of the present inhalation device further comprises a piston. The interior space of the cylindrical part as described above has a defined cross section, typically with a diameter within the range of from about 0.5 mm to about 10.0 mm, preferably from about 1 mm to about 3 mm, and particularly preferred from about 1.5 mm to about 2.5 mm, and is configured to receive an end portion of said piston. The cross section of the piston preferably substantially matches the cross section of said interior space. One or more sealings or gaskets can be present to minimize loss of liquid and pressure through the small, yet unavoidable space between piston and interior space of the cylindrical part. If such a component is present, preferably the cross sections are designed accordingly.

Further, said cylindrical part and said piston of the pumping unit are linearly moveable relative to one another such as to form a pumping chamber having a variable volume, depending on the position of the piston within the cylindrical part. Thus, by altering the volume, the pressure inside said pumping chamber is altered accordingly. Both cases are possible, namely a stationary cylindrical part and a movable piston, as well as a moveable cylindrical part and a stationary piston. In preferred embodiments of the present inhalation device, however, the pumping unit comprises a stationary or fixed piston and a moveable cylindrical part.

The inhalation device of the present invention further comprises a valve or, more specifically a check valve which may be fluidically arranged between the reservoir and the pumping unit and/or between the pumping unit and the nozzle such as to allow liquid flow in the downstream direction and prevent liquid flow in the opposite direction. In other words, the check valve serves for establishing a desired flow direction of liquid from the reservoir to the nozzle (i.e. downstream direction).

The check valve comprises a moveable body and a seat arranged upstream the body. The seat is arranged at a downstream opening of a hollow seat extension section having also an upstream opening. The medically active liquid must be able to flow into the upstream opening of the hollow seat extension section, through the same, and leave it at the downstream opening which enters the valve seat. The downstream opening could also be described to form an upstream opening of the seat, since they are fluidically connected to each other.

Unlike known valves used for inhalation devices in general, and pumping chambers of the described type, specifically for inhalation devices having a pumping unit with a fixed piston, according to the invention, the check valve's body comprises on its side facing the seat a protrusion which extends towards the reservoir through the seat and past said downstream opening of an upstream arranged "hollow seat extension section" with an according upstream opening. This means that the region which forms the actual valve seat is preceded by a hollow section, the walls of which being preferably formed by solid material, e.g. by the same material from which the seat is formed. In further preferred embodiments, the hollow section or, more specifically, the walls of the hollow section and the valve seat are formed integrally, or in other words, as a one-piece unit.

Further, the protrusion is dimensioned to leave a gap between its lateral surface and the inside of said seat extension section. This means that liquid can flow through said extension due to presence of the gap, since the protrusion is accordingly thinner than the width of the opening.

Eventually, the upstream end of said protrusion is configured to physically or mechanically interact with an upstream end, or upstream end region or surface, of said hollow seat extension section such as to being blocked from entering the hollow seat extension section, thus limiting movement of the body in downstream direction, wherein "mechanically" refers to all kinds of interaction that result in the desired limitation, regardless of actual physical surface contact. For example and as described in further detail below, in this context also magnetic forces may be suitable to provide for such physical or mechanical interaction. This means that the valve body cannot take any arbitrary distance away from the closed position in which it is in contact with the seat. In fact, its movement, and more precisely, the maximum distance between body and seat, is delimited, typically to a maximum distance within the range of from about 0.01 mm to about 5 mm, preferably of from about 0.1 mm to about 2 mm, and particularly preferred from about 0.5 mm to about 1.5 mm.

Contrary to known solutions, this movement is not limited by the known "cage" construction, i.e. a component or feature which is arranged downstream the working region, but, according to the invention, upstream of the same. Further, to implement the described check valve of the inhalation device of the invention, not the working region of the valve must be modified, but only the valve body, since the protrusion is a feature which is an integral part of the body. By control of the length of the protrusion, the range of motion of the valve body and thus, the dead volume, can be adjusted, e.g. to be as small as possible.

Although the protrusion extends through the hollow seat extension region and the seat, resulting in a possible slight increase of fluid resistance through the valve, it should be understood that valve body and protrusion do never (completely) block or interrupt liquid flow in downstream direction.

Hence, since the sufficiently precise fabrication of a valve body with protrusion is easily to achieve using available fabrication techniques, the check valve provides a precisely controllable, stable size of working region without the need of modifying said region. Thus, the dead volume can easily be minimized which is of particular importance when used in an inhalation device for the administration of a medically active liquid as in the present invention. Also, no additional working steps are required in order to manufacture or assemble the improved check valve, since the body is simply inserted into the seat, where the mechanical interaction is established automatically, as will be described further below.

In the context of the inhalation device of the present invention, another advantage of the check valve as described above is that the presence of the protrusion serves as a means for guiding the body by allowing the protrusion to slide along the inner walls of the hollow seat extension section. Since the body is attached to the protrusion, the risk of canting the body is reduced, in contrast to a body which freely floats against a mechanical stop. In the known art, a body providing sufficient safety against canting must have a cross section which is almost as large as its surrounding space in order to be guided; however, if the remaining gap to said space is too small, i.e. only tenths or hundredths of microns, the flow resistance becomes undesirably high.

According to a specific embodiment, the check valve as described above is fluidically arranged between the reservoir and the pumping unit. In this way, the valve prevents backflow of liquid from the pumping chamber into the reservoir; in particular, during the high-pressure phase. Without such a valve, part of the liquid that is present inside the pumping chamber would be lost for the actual inhalation process, which clearly is undesired. Especially in cases in which the pumping unit of the inhalation device of the present invention comprises a stationary or fixed piston and a moveable cylindrical part as described above, a check valve as comprised by the present inhalation device may be particularly advantageous: As all components of the check valve limiting the movement of the valve body, such as the protrusion of the valve body or the seat extension section are located upstream of the valve body, the dead space between the valve when used as an inlet check valve and the movable pumping chamber can be minimized or completely precluded.

In further specific embodiments which may be combined with the aforementioned one, the check valve may be fluidically arranged between the pumping unit and the nozzle. In this embodiment, the check valve serves for avoiding a backflow of liquid or ambient air from the nozzle into the pumping chamber when the refilling phase takes place which is characterized in an under-pressure inside the pumping chamber. Without a valve, the under-pressure provided by the pump would not only result in refilling the chamber with fresh liquid from the reservoir, but also with undesired air or spilled droplets from the exit of the nozzle, reducing the efficiency of the refilling process and leading to possible contamination of the interior of the volumes upstream the nozzle.

According to further embodiments, the upstream end of the protrusion of the check valve comprised by the inhalation device of the present invention comprises at least one flexible, e.g. hook-like structure which is configured to be elastically deformable such as to fit, when in the deformed state, within the hollow seat extension section, and to permanently unfold when arranged past said hollow seat extension section such that the upstream end extends laterally beyond the width of the upstream opening of the hollow seat extension section. In other words, the end of the protrusion can be temporarily folded or compressed in order to be insertable into said hollow seat extension section when the valve is assembled, i.e. by pushing the protrusion through seat and subsequent hollow seat extension section. When the valve body is sufficiently close to its seat, due to an accordingly dimensioned length of the protrusion, the structure will automatically unfold since it has now passed the region of restricted width (hollow seat extension region), now being located in front, i.e. upstream, of the upstream opening of the hollow seat extension section where sufficient space is available. After having once unfolded, however, according to these embodiments of the present invention, the structure is no longer able to slide back into the upstream opening without exerting excessive force which is not present during normal use. The structure stays in the unfolded state, unless excessive forces are provided that do not occur during normal use.

The shape and material of the end of the protrusion can be such that it is permanently deformed (damaged) when nevertheless being pulled back through the opening. It can also be configured such that it will not permanently be deformed; so, servicing the valve is possible, followed by a re-assembly of its parts. In this way, if necessary, the valve body can be exchanged without the risk of damaging the seat and/or the seat extension region during disassembly.

In another embodiment, a ring- or rod-like structure may be attached to the upstream end of the protrusion of the check valve which increases the overall lateral size of the upstream end such that it is larger than the width of the opening. The structure as an additional component can be firmly attached to the end after the protrusion has been guided through the hollow seat extension section. In this way, the design of the upstream end containing the additional component allows for a larger difference of size (e.g. diameter) of the hollow seat extension section on one hand, and size of the component of the other, since the component must not fit, during assembly, inside the hollow seat extension section. Therefore, it can also be made of a rigid, inflexible material, and/or have a size that will, despite any possible flexibility, not fit inside the hollow seat extension section.

In yet another embodiment, the upstream end of the protrusion of the check valve may be configured to provide a magnetic force which counteracts an accordingly dimensioned magnetic force arranged inside the hollow seat extension section and/or at the upstream end of the hollow seat extension section, such that the balance of the magnetic forces limits the movement of the body. In other words, instead of forces resulting from a mechanical contact of distinct parts, magnetic forces prevent the valve body from passing beyond the desired maximum position that allows for a sufficiently small fluid resistance during the low pressure phase, while providing a smallest possible dead volume when switching to the high pressure phase. For the avoidance of doubt, such magnetic forces as described above, in the context of the present invention are to be understood as a mechanical interaction.

If desired, the magnetic force can easily be adjusted such that the valve opens only after a minimal (positive) pressure threshold is exceeded, i.e. a sufficiently high-pressure difference between reservoir and pumping chamber, or pumping chamber and nozzle, respectively. So, during storage of the inhalation device, the valve may be permanently closed;

while the force necessary for opening the same during refilling the pressure chamber is very low (but not zero), only little extra energy (pressure loss) is required for its opening. The same may be true when the valve is arranged before the nozzle; it may open already at the very beginning of the high pressure phase, but may keep the duct closed during storage.

The protrusion can then e.g. be rod-shaped, making any increase of its size at its upstream end obsolete, since even the rod-like part itself can be designed to provide said magnetic forces.

In other embodiments, the described threshold feature may be realized by means of an elastic element, such as a tension or compression spring, more specifically a spiral spring or an elastic polymeric element such as a rubber element, or a pressurized hydraulic or pneumatic actuator which is accordingly dimensioned and positioned between upstream end of the hollow seat extension section and upstream end of the protrusion.

In yet another embodiment, said elastic element may be arranged at the downstream side of the hollow seat extension, pulling or pushing the body against the seat. The spring force provided by such an elastic element should be small with respect to the drag force that is provided by the liquid when streaming contrary to said spring force, e.g. less than 20%, preferably less than 10%, and particularly preferably less than 5% of the drag force provided by the streaming liquid.

According to further embodiments, the diameter of the valve body amounts to about 1 mm±0.3 mm, and/or the length of the protrusion amounts to about 0.5 mm±0.4 mm, and/or the gap has a width between 50 μm and 1000 μm, and preferably between 100 μm to 300 μm, and/or the upstream end laterally surpasses the opening with at least about 0.5 mm. The pumping chamber preferably has a diameter between about 0.5 mm and about 10 mm, and preferably between about 1 mm and about 3 mm. The length of the pumping chamber ranges preferably from about 0.5 mm to about 50 mm, and preferably of about 2 mm to about 25 mm, and particularly preferred from about 5 mm to about 20 mm. The dead volume of the check valve is preferably lower than 500 μm$^3$, and is preferably selected within the range of from about 0.001 μm$^3$ to about 100 μm$^3$, and particularly preferred within the range from about 0.01 μm$^3$ to about 1 μm$^3$.

In specific embodiments, with regard to a single dose of the medically active liquid to be administered by the inhalation device according to the present invention, the percentage of the dead volume of the check valve amounts to less than 10%, and preferably to less than 2%, and particularly preferred to less than 1% of the volume of said dose.

In further specific embodiments, the flow rate of the medically active liquid through the open valve is selected within a range of from about 1 μl/sec to about 100 μl/sec. In further specific embodiments, the check valve comprised by the inhalation device of the present invention or, more specifically the dynamics of the check valve, allows an open and closing time of up to 100 msec, such as from about 1 msec to about 50 msec.

As mentioned above, the inhalation device according to the present invention comprises a housing, which may preferably be shaped and dimensioned such that it can be held with one hand and can be operated by one finger, e.g. the thumb. Accordingly, in specific embodiments, the inhalation device or inhaler according to the present invention may be a hand-held device. The inhalation device comprises a reservoir for storage of a medically active liquid as described in further detail below that may be located inside the housing.

The inhalation device according to the invention may comprise a reservoir which may be collapsible. In specific embodiments, the reservoir may have elastic or at least limp walls that may buckle during proceeding emptying, so that the under pressure which is necessary for extraction of a certain amount of the medically active liquid is not, or almost not, increased. In alternative embodiments, the reservoir may be a rigid container having a moveable bottom by means of which the interior volume of the reservoir can also be successively be reduced.

Further, the inhalation device, as described above, may comprise a pumping unit with a pumping chamber within the housing for generation of the desired pressure which is necessary for emitting the medically active liquid and nebulizing the same. The pumping unit can also comprise additional components, such as a push button, locking device, etc.

The pumping unit may comprise a hollow piston, and a cylindrical part being adapted to house at least one end of the piston preferably a fixed piston as described above, wherein cylindrical part and said piston are linearly moveable relative to one another such as to form aforesaid pumping chamber having a variable volume.

The pumping chamber may be fluidically connected to the reservoir as described above by means of an inlet check valve as described in detail above. The check valve may serve for allowing inflow of the medically active liquid into the pumping chamber and may block a back flow of the medically active liquid into the reservoir upon release of a locking mechanism. An outlet check valve may also be present in order to prevent liquid or ambient air from flowing back through the nozzle into the pumping unit.

Downstream said pumping unit, at least one nozzle may preferably be arranged that serves for the nebulization of the liquid which is pressurized by means of the pumping unit Preferably, the nozzle is of the impingement-type, having at least two ejection channels arranged such as to eject at least two jets of a medically active liquid as further described below along respective ejection trajectories which intersect with one another at a collision point.

In specific embodiments, the inhalation device for the inhalative administration of an aerosol of a medically active liquid according to this aspect of the invention comprises a medically active liquid in form of a pharmaceutical composition comprising at least one active pharmaceutical ingredient (API), more specifically at least one inhalable active pharmaceutical ingredient which may preferably be selected from long-acting muscarinic antagonists (LAMA), long-acting beta antagonists (LABA) and inhalable glucocorticosteroids (ICS), as well as from analgetics and antidiabetics, either alone or in combination which each other.

Examples for long-acting muscarinic antagonists (LAMA) comprise, but are not limited to aclidiniumbromid, glycopyrronium salts, such as glycopyrroniumbromide, revefenacin, tiotropium, such as tiotropiumbromide, umeclidiniumbromide, oxitropiumbromide, flutropiumbromide, ipratropiumbromide, trospiumchloride, tolterodine.

Examles for long-acting beta agonists (long-acting beta adrenoceptor agonists, LABA) comprise, but are not limited to, albuterol, arformoterol, bambuterol, bitolterol, broxaterol, carbuterol, clenbuterol, fenoterol, formoterol, hexoprenaline, ibuterol, indacaterol, indacterol, isoetharine, isoprenalinelevosalbutamol, mabuterol, meluadrine, metaproterenol, olodaterol, orciprenaline, pirbuterol, procaterol, reproterol, rimiterol, ritodrine, salmeterol, salmefamol, soterenot, sulphonterol, tiaramde, terbutaline, terbuterol.

Examples of inhalable glucocorticosteroids (ICS) comprise, but are not limted to, prednisolone, prednisone, butixocortpropionate, flunisolide, beclomethasone, triamcinolone, budesonide, fluticasone, mometasone, ciclesonide, rofleponide, dexamethasone, etiprednol-dichloroacetat, deflazacort, etiprednol, loteprednol, RPR-106541, NS-126, ST-26.

Furthermore, active pharmaceutical ingredients may be selected from analgetics, such as opioid analgetics (e.g. morphine, fentanyl) or non-opiod analgetics (salicylic acid derivates e.g. acetylsalicylic acid) or cannabinoids (Tetrahydrocannabinol), antidiabetics, such as insulin.

The medically active liquid or liquid pharmaceutical composition to be nebulized or aerosolized by the present inhalation device may comprise at least one active pharmaceutically ingredient as described above, but may also comprise a mixture of two or more active pharmaceutically ingredients that may be administered by inhalation.

The medically active liquid or pharmaceutical composition to be administered by the inhalation device according to the invention is preferably formulated as a composition that is suitable, and adapted for inhalative use, in other words a composition that may be nebulized or atomized for inhalation and that is physiologically acceptable for inhalation by a subject.

The medically active liquid or pharmaceutical composition to be administered by the inhalation device of the invention or contained within the inhalation device and reservoir may be in the form of a dispersion, for example a suspension with a liquid continuous phase, and a solid dispersed phase or in the form of a solution.

In further embodiments, the medically active liquid or pharmaceutical composition may comprise, optionally, one or more physiologically acceptable excipients, which are suitable for inhalative use. Excipients which may be featured in the composition may include, but are not limited to, one or more buffering agents to regulate or control pH of the solution, salts, taste-masking agents, surfactants, lipids, antioxidants, and co-solvents, which may be used to enhance or improve solubility, for example ethanol, or a glycol.

In specific embodiments, the liquid compositions to be administered by the inhalation device of the present invention are essentially free of a propellant.

In further specific embodiments, the medically active liquid or liquid composition may be an aqueous solution, in which one or more active pharmaceutical ingredients as described above are dissolved or solubilized in a liquid carrier solution comprising water. Such aqueous solutions optionally may also comprise one or more excipients as described above.

It should be noted that all embodiments, features and combinations thereof as described above in connection with the inhalation device of the first aspect of the invention apply to the further aspects of the invention accordingly.

In a second aspect, the present invention relates to the inhalation device according to the first aspect of the invention as described above for use in the treatment or prevention of a respiratory disease, disorder or condition by inhalative administration of an aerosol of a medically active liquid as described above. In particular, the inhalation device according to the invention may be used for the treatment or prevention of a lung disease or condition. As understood herein, a lung disease, disorder or condition may affect one or more anatomical aspect and/or function of a subject's lung(s) and associated respiratory air passages.

The term "treatment" as used herein refers to the administration of the medically active liquid or pharmaceutical composition for the therapy of the lung disease, disorder or condition, for example leading to ameliorating, decreasing, or relieving of at least one symptom of the disease or condition, or stopping or slowing the progression of at least one symptom of the disease, disorder or condition, such as preserving lung function. The term "prevention" as used herein, e.g. of a lung disease or condition, may be understood to be prophylactic treatment, and refers to the administration of the medically active liquid or pharmaceutical composition to a subject that may not have developed such disease, e.g. the lung disease, disorder or condition but is at risk, or susceptible to the disease, disorder or condition.

In both, the treatment and prevention of the respiratory disorders or lung disease, disorder or condition, the medically active liquid or pharmaceutical composition may be administered by means of the inhalation device and embodiments described herein at therapeutically effective amounts.

In specific embodiments, the respiratory disorder may be a lung disease, disorder or condition such as asthma and/or chronic obstructive pulmonary disease (COPD), especially COPD. In further specific embodiments, the lung disease, disorder or condition may be an interstitial lung disease affecting the interstitium of the lung and lung tissues such as those associated with the air passages and/or air sacs (alveoli), for example pulmonary fibrosis, interstitial pneumonias, or sarcoidosis.

In a third aspect, the present invention provides for the use of an inhalation device according to the first aspect of the invention as described above in the treatment or prevention of a respiratory disease, disorder or condition by inhalative administration of an aerosol of a medically active liquid or pharmaceutical composition as described above.

In specific embodiments also of this aspect of the invention, the respiratory disease, disorder or condition may be a lung disease, disorder or condition, specifically asthma and/or chronic obstructive pulmonary disease (COPD), or an interstitial lung disease, such as pulmonary fibrosis, in particular, idiopathic pulmonary fibrosis (IPF).

In a further aspect, the present invention also refers to the use of an inhalation device according to the second aspect of the invention, for the prevention or treatment of a respiratory disease, disorder or condition as described above.

In a fourth aspect, the present invention provides for a method of treating a subject, specifically a human subject or patient, suffering from a respiratory disease, disorder or condition or for preventing a subject from developing such respiratory disease, disorder or condition, such as a lung disease, disorder or condition, specifically asthma and/or chronic obstructive pulmonary disease (COPD), or in further specific embodiments an interstitial lung disease, such as pulmonary fibrosis, in particular idiopathic pulmonary fibrosis (IPF), the method comprising a step of administering a medically active liquid or pharmaceutical composition in nebulized (aerosolized) form to said subject using an inhalation device according to the first aspect of the invention.

In specific embodiments, the inhalation device of the first aspect of the invention used in the method of this aspect of the invention is a handheld, i.e. portable device, whereby the administration of the medically active liquid or pharmaceutical composition and actuation of the device is performed by the human subject or patient themselves directly and in accordance with prescribed instructions which may also accompany the device.

DETAILED DESCRIPTION OF THE FIGURES

In FIGS. 1 to 4, an exemplary inhalation device for medically active liquids as known from international patent application WO 2018/197730 A1 is depicted schematically and not-to-scale. FIG. 1 shows the situation prior to first use.

The inhalation device comprises a housing 1, which is preferably shaped and dimensioned such that it can be held with one hand and can be operated by one finger, e.g. the thumb (not shown). A reservoir 2 for storage of a medically active liquid L is located inside the housing 1. The depicted reservoir 2 is designed to be collapsible; that means that during proceeding emptying, the elastic or at least limp walls buckle, so that the under-pressure which is necessary for extraction of a certain amount of liquid L is not, or almost not, increased. A similar effect can be achieved when a rigid container has a moveable bottom by means of which the interior volume of the reservoir 2 can also be successively be reduced (not shown).

Further, the inhalation device comprises a pumping unit 3 with a pumping chamber 3D within the housing 1 for generation of the desired pressure which is necessary for emitting liquid L and nebulizing the same. The pumping unit 3 can also comprise additional, not depicted components (push button, locking device, etc.).

The pumping unit 3 comprises a hollow cylindrical part 3A and a piston 3B, the cylindrical part 3A having an interior space 3C configured to receive an end portion 3B' of said piston 3B, wherein said cylindrical part 3A and said piston 3B are linearly moveable relative to one another such as to form a pumping chamber 3D having a variable volume.

Pumping chamber 3D is fluidically connected with reservoir 2 by means of an inlet check valve 4. Check valve 4 serves for allowing inflow of liquid L into the pumping chamber 3D and blocks a back flow of liquid L into reservoir 2 upon release of the not-depicted locking mechanism.

In other words, piston 3B can at least partially be pushed into hollow cylindrical part 3A, resulting in a decrease of the interior volume of pumping chamber 3D. The term "interior volume" describes that volume which extends from the reservoir-facing inlet of the pumping chamber 3D where valve 4 is arranged to the place where the upstream end of piston 3B is located, and where an additional outlet valve 7 is placed. In the depicted situation in FIG. 1, piston 3B is almost entirely contained in hollow cylindrical part 3A. As a result, the interior volume of pumping chamber 3D, situated between check valve 4 and the upstream end of piston 3B, is at a minimum.

As a means for the storage of potential energy 6, a spring is provided which is coupled with one (upwards directed) end to the hollow cylindrical part 3A and which is supported at housing 1 (lower part of the figure).

Preferably, in the region which serves for the reception of piston 3B, pumping chamber 3D has a circular inner cross section that corresponds to the (then also) circular outside cross section of the according piston's section. Of course, other cross section shapes are possible as well.

According to the depicted embodiment, check valve 4 is arranged between reservoir 2 and inlet of pumping chamber 3D.

Also depicted is an optional outlet valve 7 inside piston 3B for avoiding back flow of liquid L or air into the exterior end of piston 3B from the outside. Outlet valve 7 is arranged in the interior end of piston 3B. Liquid L can pass outlet valve 7 in direction of nozzle 5, but outlet valve 7 blocks any undesired back flow in the opposite direction.

Finally, the inhalation device comprises a nozzle 5 which is connected liquid-tight to an exterior, downstream end of piston 3B. Nozzle 5 can be any known nozzle which is suitable for nebulizing/atomizing liquid. The nozzle 5 which is depicted as an example uses the principle of nebulization by means of two colliding liquid jets. Preferably, the cross sections of the liquid-containing channels are relatively small, and typically, in the region of microns.

As can be seen in FIG. 1, in the depicted example, piston 3B is designed immobile and firmly attached to housing 1, indicated by the connection in the region of its exterior end with housing 1. Piston 3B is also firmly attached to nozzle 5, which in turn is attached to housing 1 as well. On the contrary, hollow cylindrical part 3A is designed to be moveable with respect to housing 1 and nozzle 5. It is noted that the invention can be used as well in the case of an immobile hollow cylindrical part 3A and a moveable piston 3B.

Figure 2:
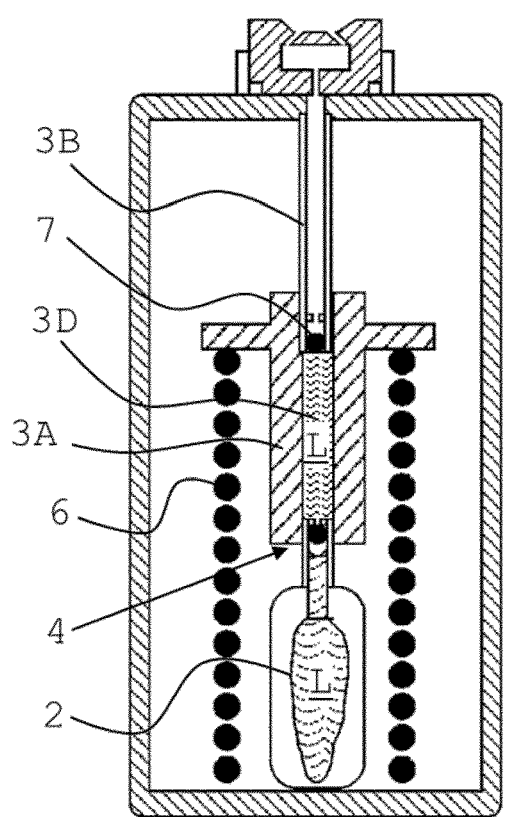
FIG. 2 shows the embodiment of FIG. 1 before initially filling the pumping chamber.

FIG. 2 in which some of the already introduced reference numerals have been omitted, shows the embodiment of FIG. 1 when initially filling pumping chamber 3D. Hollow cylindrical part 3A is pulled down, loading the means for the storage of potential energy 6. Outlet valve 7 is closed due to under-pressure inside pumping chamber 3D, and check valve 4 is open to reservoir 2. In the following, this situation is also referred to as the "low pressure phase". Increasingly collapsing walls of reservoir 2 allow its inside pressure remain nearly constant, while pressure inside pumping chamber 3D drops because of the downwards motion pulling hollow cylindrical part 3A off piston 3B, increasing the interior volume of pumping chamber 3D. As a result, pumping chamber 3D fills with liquid L from reservoir 2.

Figure 3:
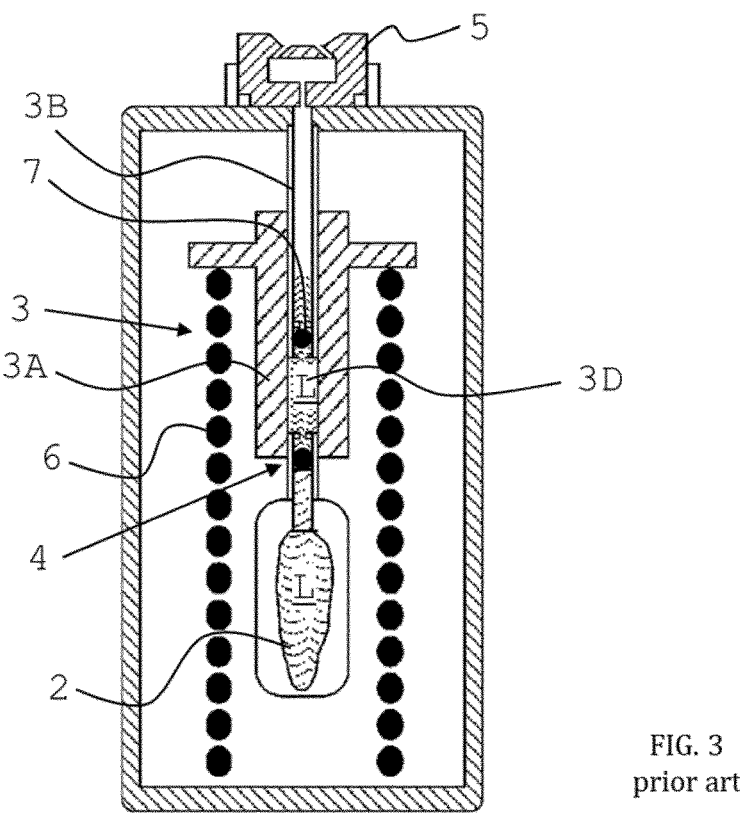
FIG. 3 shows the situation during the first activation.

In FIG. 3, the situation during the first activation of the inhalation device is shown. Means for the storage of potential energy 6 has been released from the loaded position as shown in FIG. 2. It pushes hollow cylindrical part 3A comprising pumping chamber 3D onto piston 3B, the interior end of which coming closer to check valve 4 now being closed. As a result, the pressure inside pumping chamber 3D rises and keeps inlet valve 4 in the closed position, but opens outlet valve 7. Liquid L rises inside piston 3B towards its exterior end and nozzle 5. This situation is also referred to as the "high pressure phase".

Figure 4:
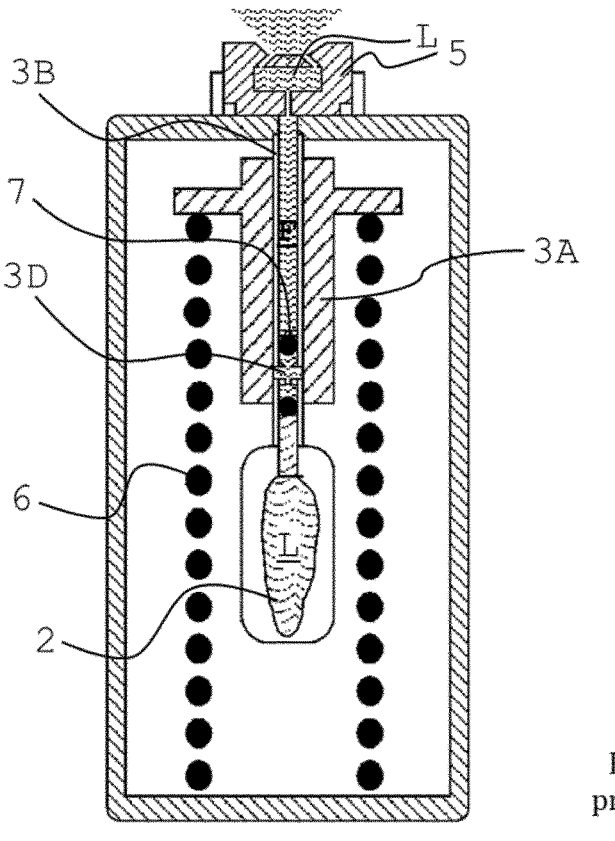
FIG. 4 shows the situation at the end of the first activation.

FIG. 4 shows the situation at the end of the first (or any subsequent) activation. Means for the storage of potential energy 6 is in its most relaxed end position (spring fully extended). Also, hollow cylindrical part 3A has been pushed almost entirely onto piston 3B such that the interior volume of pumping chamber 3D reaches its minimum. Most of liquid L previously contained inside pumping chamber 3D has passed outlet valve 7 into piston 3B. Liquid L already contained within piston 3B has been pushed towards, and through, nozzle 5, where the desired nebulization takes place, producing a spray or, more specifically, the aerosol to be administered. This situation is also referred to as the "emission phase" which is also part of aforesaid "high pressure phase".

As indicated in FIGS. 1 to 4, both check valves 4, 7 are designed as ball valves having a seat and a cage like obstruction to delimit movement of the ball in downstream direction.

Figure 5:
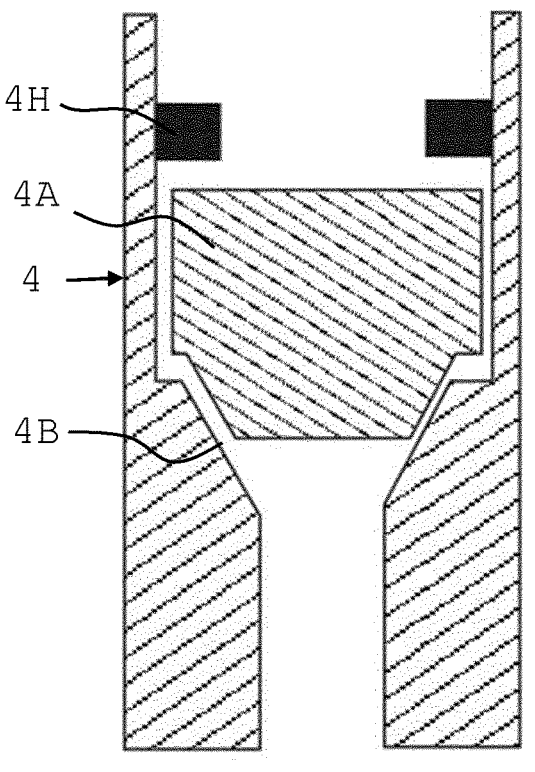
FIG. 5 shows a schematic of the cross section of a valve known in the art.

In FIG. 5, a schematic of the cross section of a valve for inhalation devices is shown. For the sake of clarity, liquid is not shown in the drawing. The desired flow direction points upwards in this and the following pictures.

The valve 4 comprises a body 4A which is adapted to fit in a seat 4B. Body 4A is moveable in vertical direction. A ring 4H is fixedly inserted downstream body 4A in order to delimit movement of the latter. When body 4A is in its most downstream position (not depicted), the vertical distance between its upstream side and seat 4B defines the afore-mentioned dead volume.

Body 4A is exemplarily shown as a cylinder with an upstream end that has the shape of a truncated cone, and seat 4B is accordingly funnel shaped. However, body 4A could also have the shape of a full or semi sphere, and the seat 4B could have an accordingly shaped design. It should be noted that this also applies for the bodies and seats discussed in the following figures.

Figure 6:
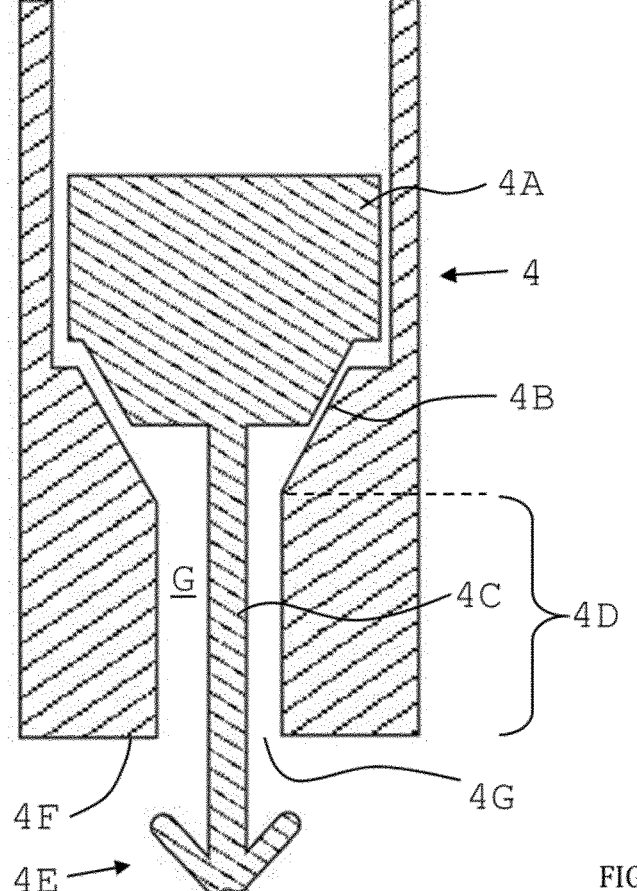
FIG. 6 shows a schematic of the cross section of a first embodiment of a check valve comprised by the inhalation device according to the invention.

FIG. 6 shows a schematic of the cross section of a first embodiment of a check valve comprised by the inhalation device according to the invention. In addition to the features known from the art and already shown in the previous figure, to the upstream side of body 4A, a protrusion 4C is attached.

Protrusion 4C extends in upstream direction towards the reservoir (not shown) through seat 4B, having an opening, and past an upstream arranged hollow seat extension section 4D having a downstream opening (no reference numeral) facing the, and being fluidically connected to, the seat 4B, and an upstream opening 4G arranged at the opposite, upstream end of the hollow seat extension region 4D. The protrusion 4C is dimensioned to leave a gap G between its lateral surface and the inside of hollow seat extension section 4D. Furthermore, upstream end 4E of protrusion 4C is configured to mechanically interact with an upstream end 4F of said hollow seat extension section 4D such as to being blocked from (re-)entering the latter when pulled or pushed in downstream direction, thus limiting movement of body 4A in said direction.

In the depicted embodiment, upstream end 4E of protrusion 4C comprises at a flexible hooklike structure which is configured to be elastically deformable such as to fit, in the deformed state (not depicted), within the hollow seat extension section 4D, since in the unfolded state, it is only slightly wider than the width of upstream opening 4G and the subsequent interior space of hollow seat extension section 4D. As shown, said structure takes an unfolding state when arranged past said hollow seat extension section 4D, and more precisely, past its upstream end 4F. As a result, upstream end 4E of protrusion 4C extends laterally beyond the width of the upstream opening 4G of the hollow seat extension section 4D, and movement of body 4A in downstream direction is limited.

In FIG. 7, a schematic of the cross section of a second embodiment of a check valve 4 comprised by the inhalation device according to the invention is depicted. In this embodiment, the upstream end 4E of protrusion 4C receives a detachable ring-like structure 4I which increases the overall lateral size of upstream end 4E such that it is larger than the width of the upstream opening 4G. As a result, movement of protrusion 4C is blocked when ring-like structure 4I touches the upstream end 4F of hollow seat extension section 4D, and thus, valve body 4A is stopped from moving further away from seat 4B.

In FIG. 8, another embodiment of the check valve 4 to be comprised by the inhalation device of the present invention is schematically depicted. In this embodiment, the upstream end 4E of protrusion 4C is configured to provide a magnetic force, stemming from a first magnet 4J, which counteracts an accordingly dimensioned magnetic force arranged inside hollow seat extension section 4D at the upstream end 4F thereof, such that the balance of magnetic forces limits the movement of the body 4A. In the picture, a black rectangle indicates a "north pole" of a magnet, and a white rectangle indicates a "south pole". For the avoidance of doubt, it should be mentioned that the opposite arrangement of "poles" would result in the same desired effect. As can be seen in the picture as well, the protrusion 4C can be pulled through the hollow seat extension section 4D without damaging any of the surfaces; however, during normal use, the drag of the flowing liquid (not depicted) onto the moveable parts must be always lower than the force needed to overcome the holding force provided by the magnets 4J, 4K.

One of the advantages of this embodiment is the possibility of servicing or exchanging the valve body 4A.

FIGS. 9 and 10 show another embodiment of the upstream end 4E of protrusion 4C of the check valve to be comprised by the present invention. A structure that consists of beams arranged along the edges of a two- or three-dimensional rhombus which forms the end 4E of protrusion 4C can be deformed perpendicular to the longitudinal direction of protrusion 4C (FIG. 10). The angles, stiffness etc. of the structure can be selected to withstand a too strong deformation during normal use, so that the mechanical interaction is always provided. However, when, e.g. for servicing, the valve body (not shown) is strongly pulled, the rhombus shaped structure is deformed so that the protrusion 4C can be pulled through the hollow seat extension region (not shown). Also, a re-insertion is possible. When in the undeformed state, the structure has a lateral size that provides the desired mechanical interaction with the upstream end 4F of the seat extension section 4D (not shown).

LIST OF REFERENCE NUMBERS 1 housing
2 reservoir
3 pumping unit
3A hollow cylindrical part
3B piston
3B' end portion (of piston)
3C interior space
3D pumping chamber
4 valve, inlet valve
4A valve body, body
4B valve seat, seat
4C protrusion
4D seat extension section
4E upstream end (of the protrusion)
4F upstream end (of the seat extension section)
4G upstream opening (of the seat extension section)
4H ring
4I ring-like structure
4J first magnet
4K second magnet
5 nozzle
6 means for the delivery of mechanical energy
7 check valve, outlet valve
L liquid
G gap The following is a list of numbered embodiments E1 to E14 which are comprised by the present invention:

E1. Valve (4) for an inhalation device for generation of an aerosol of a medically active liquid, said inhalation device comprising:
    a housing (1), inside this housing (1) a reservoir (2) for storing said medically active liquid (L), downstream this reservoir (2) a pumping unit (3) for generation of a pressure connected to a means for the delivery of mechanical energy (6) to said pumping unit (3), and downstream said pumping unit (3) a nozzle (5);

wherein the pumping unit (3) comprises a hollow cylindrical part (3A) and a piston (3B), the cylindrical part (3A) having an interior space (3C) configured to receive an end portion (3B') of said piston (3B), wherein said cylindrical part (3A) and said piston (3B) are linearly moveable relative to one another such as to form a pumping chamber (3D) having a variable volume;

the inhalation device further comprising a check valve (4) such as to allow liquid (L) flow in the downstream direction and prevent liquid (L) flow in the opposite direction, the valve (4) comprising a moveable body (4A) and a seat (4B) arranged upstream the body (4A), the seat (4B) being arranged at a downstream opening of a hollow seat extension section (4D) having an upstream opening (4G), and wherein the check valve's body (4A) comprises on its side facing the seat (4B) a protrusion (4C) which extends through the seat (4B) and past said upstream opening (4G) of said seat extension section (4D), the protrusion (4C) being dimensioned to leave a gap (G) between its lateral surface and an inside of said hollow seat extension section (4D), wherein further, the upstream end (4E) of said protrusion (4C) is configured to mechanically interact with an upstream end (4F) of said hollow seat extension section (4D) such as to being blocked from entering said hollow extension section (4D), thus limiting movement of the body (4A) in downstream direction.

E2. Valve (4) according to embodiment E1, wherein the same is fluidically arranged between the reservoir (2) and the pumping unit (3).

E3. Valve (4) according to embodiment E1, wherein the same is fluidically arranged between the pumping unit (3) and the nozzle (5).

E4. Valve (4) according to any of embodiments E1 to E3, wherein the upstream end (4E) of the protrusion (4C) comprises at least one flexible structure which is configured to be elastically deformable such as to fit, in a deformed state, within the hollow seat extension section (4D), and to permanently unfold when arranged past said hollow seat extension section (4D) such that said upstream end (4E) extends laterally beyond a width of the upstream opening (4G) of the hollow seat extension section (4D).

E5. Valve (4) according to any of embodiments E1 to E3, wherein a ring- or rod-like structure is attached to the upstream end (4E) of the protrusion (4C) which increases the overall lateral size of the upstream end (4E) such that it is larger than the width of the opening (4G).

E6. Valve (4) according to any of embodiments E1 to E3, wherein the upstream end (4E) of the protrusion (4C) is configured to provide a magnetic force which counteracts an accordingly dimensioned magnetic force arranged inside the seat extension section (4D) and/or at the upstream end thereof, such that the balance of magnetic forces limits the movement of the body (4A).

E7. Valve (4) according to any of the preceding embodiments, wherein the diameter of the valve body (4A) amounts to 1 mm±0.3 mm, and/or the length of the protrusion (4C) amounts to 0.5 mm±0.4 mm, and/or the gap (G) has a width between 50 μm and 1000 μm, and/or the upstream end (4E) laterally surpasses the opening (4G) with at least 0.5 mm.

E8. Inhalation device for the inhalative administration of an aerosol of a medically active liquid comprising a valve according to any one of embodiments E1 to E7.

E9. Inhalation device according to embodiment E8, wherein the medically active liquid is a pharmaceutical composition comprising at least one inhalable active ingredient selected from the group consisting of long-acting muscarinic antagonists (LAMA), long-acting beta antagonists (LABA) and inhalable glucocorticoids (ICS).

E10. Inhalation device according embodiment E8 or E9 for use in the treatment or prevention of a respiratory disorder by inhalative administration of an aerosol of a medically active liquid.

E11. Inhalation device for use according to embodiment E10, wherein the respiratory disorder is a lung disease or condition.

E12. Inhalation device for use according to embodiment E10 or E11, wherein the lung disease or condition is asthma and/or chronic obstructive pulmonary disease (COPD).

E13. The use of an inhalation device according to any one of embodiments E8 or E9, for the prevention or treatment of a respiratory disorder.

E14. A method of treating a subject suffering from a lung disease or condition, specifically asthma and/or chronic obstructive pulmonary disease (COPD), the method comprising a step of administering a pharmaceutical composition in nebulized (aerosolized) form to said subject using a inhalation device according to any one of embodiments E8 to E10.

WHat is claimed is:

1. An inhalation device for generating an aerosol of a medically active liquid and for the inhalative administration of the aerosol of said medically active liquid, said inhalation device comprising:
    a housing;
    a reservoir within the housing for storing said medically active liquid;
    a pumping unit, downstream from the reservoir, for generation of a pressure and connected to a spring; and
    a nozzle downstream from the pumping unit; wherein the pumping unit comprises a hollow cylindrical part and a piston, the hollow cylindrical part having an interior space configured to receive an end portion of said piston, wherein said hollow cylindrical part and said piston are linearly moveable relative to one another such as to form a pumping chamber having a variable volume; and
    a check valve configured to allow liquid flow in a downstream direction and prevent liquid flow in an opposite direction, the check valve comprising a moveable body and a seat arranged upstream from the moveable body, the seat being arranged at a downstream opening of a hollow seat extension section having an upstream opening, and wherein the moveable body further comprises a protrusion having a solid body that extends through the seat and past said upstream opening of said hollow seat extension section, the protrusion being dimensioned to leave a gap between its lateral surface and an inside of said hollow seat extension section, wherein the protrusion has an upstream end configured to mechanically interact with an upstream end of said hollow seat extension section to delimit movement of the moveable body in a downstream direction.

2. The inhalation device according to claim 1, wherein the check valve is fluidically arranged between the reservoir and the pumping unit.

3. The inhalation device according to claim 1, wherein the check valve is fluidically arranged between the pumping unit and the nozzle.

4. The inhalation device according to claim 1, wherein the upstream end of the protrusion of the check valve comprises at least one flexible structure which is configured to be elastically deformable such as to fit, in a deformed state, within the hollow seat extension section, and to permanently unfold when arranged past said hollow seat extension section such that said upstream end of the protrusion extends laterally beyond a width of the upstream opening of the hollow seat extension section.

5. The inhalation device according to claim 1, wherein a ring-like structure is attached to the upstream end of the protrusion of the check valve which increases an overall lateral size of the upstream end of the protrusion such that it is larger than the width of the upstream opening of the hollow seat extension section.

6. The inhalation device according to claim 1, wherein the upstream end of the protrusion of the check valve is configured to provide a magnetic force which counteracts a magnet arranged inside the hollow seat extension section and/or at the upstream end thereof, such that the balance of magnetic forces limits the movement of the body.

7. The inhalation device according to claim 1, wherein a diameter of the valve body is 1 mm±0.3 mm, and/or a length of the protrusion is 0.5 mm±0.4 mm, and/or the gap has a width between 50 μm and 1000 μm, and/or an upstream end of the protrusion laterally surpasses the upstream opening of the hollow seat extension section by at least 0.5 mm.

8. The inhalation device according to claim 1, wherein the pumping unit comprises a stationary or fixed piston and a moveable cylindrical part.

9. The inhalation device according to claim 1, wherein a dead volume of the check valve is lower than 500 μm$^3$.

10. The inhalation device according to claim 1, wherein a dead volume of the check valve is selected within the range of from about 0.001 μm$^3$ to about 100 μm$^3$.

11. The inhalation device according to claim 1, wherein a flow rate of the medically active liquid through the opened check valve is selected within a range of from about 1 μl/sec to about 100 μl/sec.

12. The inhalation device according to claim 1, wherein the check valve allows an opening and closing time of up to 100 msec.

13. The inhalation device according to claim 1, wherein the medically active liquid is a pharmaceutical composition comprising at least one inhalable active ingredient selected from the group consisting of long-acting muscarinic antagonists (LAMA), long-acting beta antagonists (LABA) and inhalable glucocorticosteroids (ICS).

14. A method of treating a subject suffering from a respiratory disease, disorder, or condition; or for preventing a respiratory disease, disorder, or condition in the subject, the method comprising a step of administering a pharmaceutical composition in nebulized form to said subject using an inhalation device according to claim 1.

15. The method of claim 14, wherein the respiratory disease, disorder, or condition is a lung disease, disorder, or condition.

16. The method of claim 14, wherein the respiratory disease, disorder, or condition is asthma and/or chronic obstructive pulmonary disease (COPD).

17. The inhalation device according to claim 1, wherein the upstream end of the protrusion is smaller than the moveable body.

18. The inhalation device according to claim 1, wherein the upstream end of the protrusion has a smaller cross-sectional area than the moveable body.

19. The inhalation device according to claim 1, wherein the upstream end of the protrusion has a smaller diameter than the moveable body.

20. The inhalation device according to claim 1, wherein a rod-like structure is perpendicularly attached to the upstream end of the protrusion of the check valve which increases an overall lateral size of the upstream end of the protrusion such that it is larger than a width of the upstream opening of the hollow seat extension section.

* * * * *